(12) United States Patent
Kobayashi

(10) Patent No.: US 9,375,132 B2
(45) Date of Patent: Jun. 28, 2016

(54) MEDICAL IMAGE PROCESSING APPARATUS AND MEDICAL IMAGE DIAGNOSIS APPARATUS

(75) Inventor: Hideaki Kobayashi, Otawara (JP)

(73) Assignees: Kabushiki Kaisha Toshiba, Tokyo (JP); Toshiba Medical Systems Corporation, Otawara-shi (JP)

(*) Notice: Subject to any disclaimer, the term of this patent is extended or adjusted under 35 U.S.C. 154(b) by 176 days.

(21) Appl. No.: 13/989,916

(22) PCT Filed: Jun. 21, 2012

(86) PCT No.: PCT/JP2012/065917
§ 371 (c)(1),
(2), (4) Date: May 28, 2013

(87) PCT Pub. No.: WO2012/176854
PCT Pub. Date: Dec. 27, 2012

(65) Prior Publication Data
US 2013/0257865 A1    Oct. 3, 2013

(30) Foreign Application Priority Data
Jun. 23, 2011 (JP) ................................. 2011-139005

(51) Int. Cl.
*G06T 15/08* (2011.01)
*A61B 1/00* (2006.01)
(Continued)

(52) U.S. Cl.
CPC .............. *A61B 1/00045* (2013.01); *A61B 6/466* (2013.01); *A61B 6/5211* (2013.01); *G06T 15/08* (2013.01); *A61B 5/055* (2013.01)

(58) Field of Classification Search
None
See application file for complete search history.

(56) References Cited

U.S. PATENT DOCUMENTS 6,807,292 B1    10/2004    Goto et al.
2003/0007673 A1    1/2003    Truyen et al.
(Continued)

FOREIGN PATENT DOCUMENTS

JP    11 219448    8/1999
JP    11 318884    11/1999
(Continued)

OTHER PUBLICATIONS

Combined Office Action and Search Report issued Nov. 26, 2014 in Chinese Patent Application No. 201280004894.0 (with English translation of category of cited documents).
(Continued)

*Primary Examiner* — Kee M Tung
*Assistant Examiner* — Nicholas R Wilson
(74) *Attorney, Agent, or Firm* — Oblon, McClelland, Maier & Neustadt, L.L.P.

(57) ABSTRACT

A medical image processing apparatus including a storage, virtual endoscopic image generating unit, region identifying unit, and image generating unit. The storage stores three-dimensional images of a tubular body. The virtual endoscopic image generating unit generates, by using the three-dimensional images of the tubular body, virtual endoscopic images when an inside of a tract of the tubular body is observed based on a view point location and view direction placed inside the tract. The region identifying unit obtains an observation region and/or non-observation region based on the view point location and view direction by using the three-dimensional images. The image generating unit that generates an image that corresponds to the observation region and/or non-observation region are/is distinguishably displayed on the image obtained from the three-dimensional images.

13 Claims, 11 Drawing Sheets

(51) Int. Cl.
  *A61B 6/00*  (2006.01)
  *A61B 5/055* (2006.01)

(56) References Cited

U.S. PATENT DOCUMENTS

| | | |
|---|---|---|
| 2004/0109603 A1 | 6/2004 | Bitter et al. |
| 2007/0003131 A1 | 1/2007 | Kaufman |
| 2007/0182731 A1 | 8/2007 | Gundel |
| 2010/0085273 A1 | 4/2010 | Nakayama |
| 2010/0185094 A1 | 7/2010 | Hamada et al. |
| 2011/0018871 A1* | 1/2011 | Shirahata ..................... 345/419 |
| 2011/0255755 A1 | 10/2011 | Shirahata et al. |

FOREIGN PATENT DOCUMENTS

| | | |
|---|---|---|
| JP | 2001 143098 | 5/2001 |
| JP | 2004 522464 | 7/2004 |
| JP | 2004 529715 | 9/2004 |
| JP | 2007 195971 | 8/2007 |
| JP | 2010 82374 | 4/2010 |
| JP | 2010 167032 | 8/2010 |
| JP | 2010 274405 | 12/2010 |
| JP | 2010-284405 A | 12/2010 |
| JP | 2011 30839 | 2/2011 |
| JP | 2011 36600 | 2/2011 |
| WO | 2009 116465 | 9/2009 |
| WO | 2010 074058 | 7/2010 |

OTHER PUBLICATIONS

Kensaku Mori, et al., "A Method for Detecting Unobserved Regions in Virtual Endoscopy System", Proc. SPIE, vol. 4321, No. 40-4, Dec. 2012, pp. 134-145.

Hayashi, Y., et al., "Quantitative Evaluation of Fly-through Methods Based on Undisplayed Regions in Virtual Colonoscopy," Transactions of Japanese Society for Medical and Biological Engineering, vol. 16, No. 12, pp. 247-252, (Dec. 10, 2002) (with English abstract).

Hayashi, Y., et al., "Development of automated navigation function in the Virtualized Endoscope System," Proceedings of the 2000 IEICE General Conference, pp. 411-412, (Mar. 7, 2000).

International Search Report Issued Oct. 16, 2012 in PCT/JP12/65917 Filed Jun. 21, 2012.

Office Action issued Jan. 12, 2016 in Japanese Patent Application No. 2012-140235.

* cited by examiner

MEDICAL IMAGE PROCESSING APPARATUS AND MEDICAL IMAGE DIAGNOSIS APPARATUS

FIELD OF THE INVENTION

The embodiment of the present invention relates to medical image processing apparatus and medical image diagnosis apparatus.

BACKGROUND OF THE INVENTION

An X-ray computed tomography device (hereinafter, referred to as CT (Computed Tomography)) and other modalities thereof are used to collect three-dimensional data.

For example, a three-dimensional image in which view point is placed inside a tract of a tubular body such as the digestive tract, trachea, blood vessels, etc. may be made based on the three-dimensional data (volume data) collected from CT. Furthermore, references made to the three-dimensional image may include the three-dimensional data.

A large intestine analysis system exists for carrying out preoperative diagnosis including a screening test. For example, large intestine analysis by CT (CTC: CT colonography) is known.

In CTC, as an example, a displaying method using virtual endoscopy (VE) is used, the endoscopic observation due to virtual endoscopy (VE) being able to carry out based on the view point location placed inside the tract of the tubular body. Furthermore, the images displayed upon virtual endoscopy may be referred to as virtual endoscopic images.

Generally, upon endoscopy for intratubularly observing the large intestine, there is an unobservable region towards the interior of the tract, in which a crescent-shaped crease becomes a blind spot. This is because the view point location cannot be optionally set with endoscopy.

In contrast, with virtual endoscopy (VE), the view point location may be optionally set. In virtual endoscopy, regions that become dead spots and cannot be observed depending on the view point location (non-observation region) are generated; however, these may be become to observable regions by shifting the view point location.

Moreover, with CTC, a displaying method by multi-planar reconstruction (MPR) is used, the multi-planar reconstruction allowing extracting and displaying of an optional cross-section using the three-dimensional image. Furthermore, the image displayed by multi-planar reconstruction may be referred to as an MPR image.

In multi-planar reconstruction, the view point location upon virtual endoscopy and the presence of a lesion candidate may be comprehended by displaying the view point location upon virtual endoscopy on the MPR image.

PRIOR ART DOCUMENT

Patent Document

[Patent Document 1] Japanese published unexamined application 2010-167032

SUMMARY OF THE INVENTION

Problem to be Solved by the Invention

However, the MPR image is a cross-sectional image, so sometimes distinguishing which region is being observed upon virtual endoscopy is difficult by only displaying the view point location on the MPR image.

This embodiment solves the abovementioned problems with the purpose of providing medical image processing apparatus that may easily distinguish the observation region and non-observation region on the MPR image, along with the medical image diagnosis apparatus.

Means of Solving the Problem

In order to solve the abovementioned problems, the medical image processing apparatus of the embodiment comprises a storage, a virtual endoscopic image generating unit, a region identifying means, and an image generating unit. The storage stores three-dimensional images of a tubular body. The virtual endoscopic image generating unit generates, by using the three-dimensional images of the tubular body, virtual endoscopic images when the inside of the tract is observed based on a view point location and view direction placed inside the tract of the tubular body. The region identifying means obtains an observation region and/or non-observation region based on the view point location and view direction by using the three-dimensional images. The image generating unit that generates an image which corresponds to the observation region and/or non-observation region, the image being distinguishably displayed on the image obtained from the three-dimensional images.

DESCRIPTION OF THE PREFERRED EMBODIMENT

Next, embodiments of the medical image processing apparatus are described with reference to each diagram.

[Embodiment 1]

The medical image processing apparatus related to Embodiment 1 is described.

CT is used as an example of modality. Three-dimensional images of the tubular body are collected by the CT.

Generally, the modality is connected to PACS (Picture Archiving and Communication System), which is a system allowing for transmission and display of digital images via a network conforming to DICOM (Digital Imaging and Communications in Medicine). The three-dimensional images of the tubular body collected by the modality are transmitted to the PACS via the network. Furthermore, the three-dimensional images of the tubular body may be stored in the storage of the modality (not illustrated).

(Storage)

An example of the storage 1 storing a three-dimensional image of the tubular body is the storage of the PACS and modality. Medical image processing apparatus is connected to the storage 1. Furthermore, the storage 1 may be provided in the medical image processing apparatus.

Figure 1:
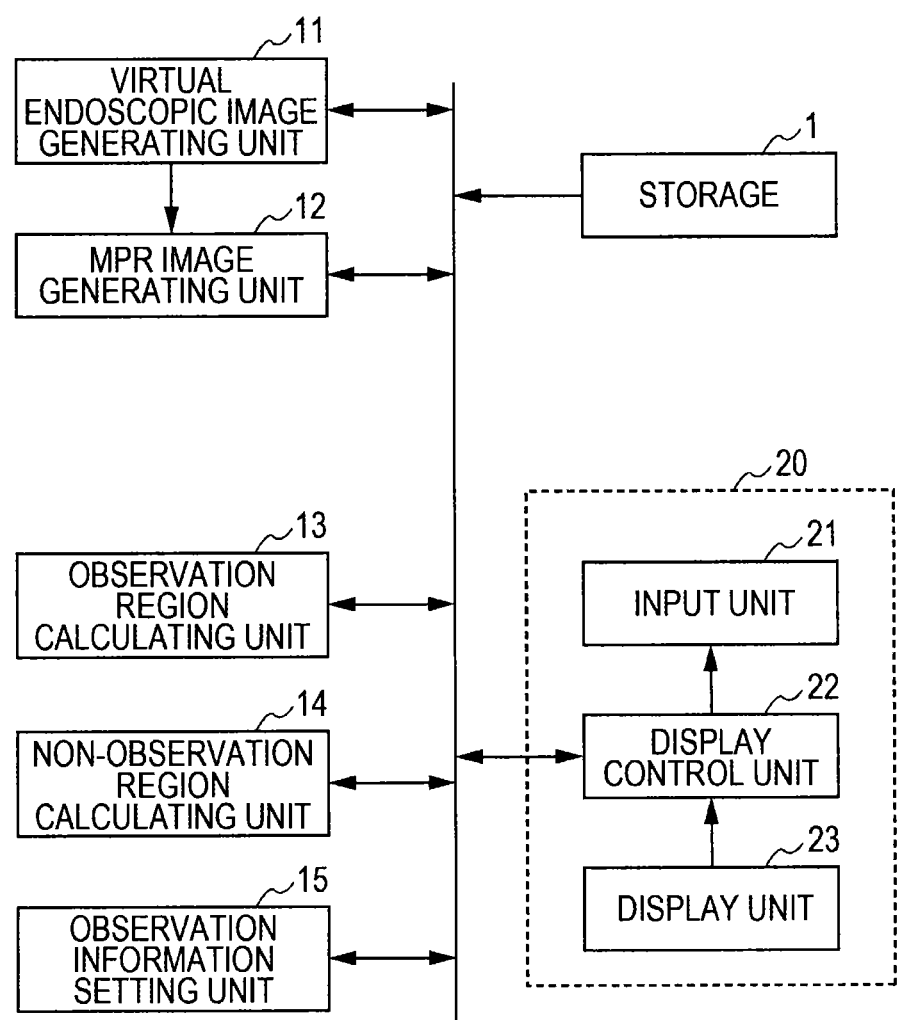
FIG. 1 is a configuration block diagram of the medical image processing apparatus related to Embodiment 1.

Next, the medical image processing apparatus is described with reference to FIG. 1. FIG. 1 is a configuration block diagram of the medical image processing apparatus.

The medical image processing apparatus comprises a virtual endoscopic image generating unit 11, an MPR image generating unit 12, an observation region calculating unit 13, a non-observation region calculating unit 14, an observation information setting unit 15, and a GUI (graphical user interface) 20. The MPR image generating unit may be simply referred to as an image generating unit. Moreover, the observation region calculating unit 13 and non-observation region calculating unit 14 may be referred to as a region identifying means.

These configurations may be realized by carrying out an image processing program in a microprocessor equipped in computer apparatus. Furthermore, an image displaying and processing program may be installed into the computer apparatus in advance. The image displaying and processing program may be stored in a storage medium (magnetic disc, magneto-optical disc, optical disc, semiconductor memory, etc.) and appropriately installed in the computer apparatus. Furthermore, the image displaying and processing program may be set such that it is distributed via the network and appropriately installed in the computer apparatus.

Furthermore, a part of or all among these configurations may be realized by hardware such as a logic circuit, etc., or a combination of the hardware and software control.

(Virtual Endoscopic Image Generating Unit)

Figure 2:
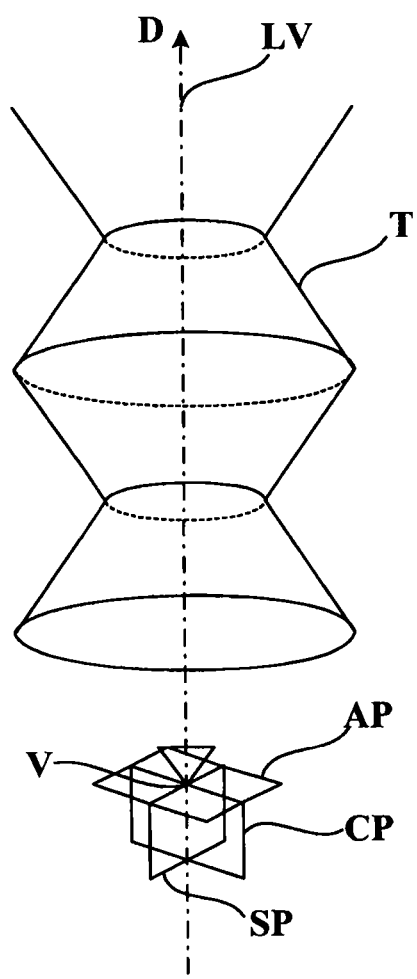
FIG. 2 is a perspective view showing the tubular body.

FIG. 2 is a perspective view showing the tubular body. In FIG. 2, the tubular body, view point location, gaze, and view direction are indicated by T, V, LV, and D, respectively.

In the same manner, the virtual endoscopic image generating unit 11 uses the three-dimensional images of the tubular body stored in the storage 1 and generates virtual endoscopic images when observing inside the tract based on the observation information including the intratubular view point location V, view direction D, and view angle VA placed inside the tract. Here, observation inside the tract refers to observation inside the tract when the virtual endoscopic images generated by the virtual endoscopic image generating unit 11 are displayed. Accordingly, the regions of blind spots, etc. that are not drawn into virtual endoscopic images are not observed.

After the three-dimensional data is collected and before switching to the generation of MPR images mentioned later, the virtual endoscopic image generating unit 11 generates the virtual endoscopic images when the inside of the tract is observed based on, for example, the view point locations placed at a prescribed interval along the core of the tubular body. The storage (for example, the internal storage of the medical image processing apparatus) associates the generated virtual endoscopic images with the observation information and stores them. Moreover, based on a view point location different from these view point locations, the virtual endoscopic image generating unit 11 generates virtual endoscopic images even after it has shifted to the generation of MPR images. At this time also, the storage associates the generated virtual endoscopic images with the observation information and stores them.

(Observation Region Calculating Unit)

Next, the observation region calculating unit 13 is described.

Along with generating the virtual endoscopic images based on the view point location by the virtual endoscopic image generating unit 11, the observation region calculating unit 13 obtains the observation region based on the position thereof. Here, the observation region of the virtual endoscopic images refers to the region inside the tubular body T as an output source of light injected into the view point location when the view point location is placed inside the tubular body T. Moreover, the non-observation region refers to the region that subtracts the observation region from the overall region inside the tubular body T.

Regarding the observation region calculating unit 13, first, a three-dimensional image of the tubular body T is obtained as a region with a pixel value corresponding to that of air, which is the largest among the closed regions. Subsequently, the observation region (three-dimensional data) is obtained using the three-dimensional image of the tubular body T based on the observation information (view point location, view direction, and view angle) on the virtual endoscopic images. Furthermore, as mentioned later, an MPR image (including the observation region as the 2-dimensional data (cross-sectional image)) is obtained based on the observation information using the observation region as the observation region (three-dimensional data). Here, the observation region comprises the region that is being observed (region being observed) among the currently displayed virtual endoscopic images and the region that was observed (region that has been observed) among the virtual endoscopic images that were displayed in the past.

As described above, the observation region (three-dimensional data) is obtained based on the observation information using the three-dimensional image of the tubular body T and subsequently, the MPR image is obtained using the observation region. However, without limiting this, the MPR image may be obtained using the three-dimensional image of the tubular body T and subsequently the MPR image (including the observation region as the 2-dimensional data (cross-sectional image)) may be obtained based on the observation information using the MPR image.

Figure 3:
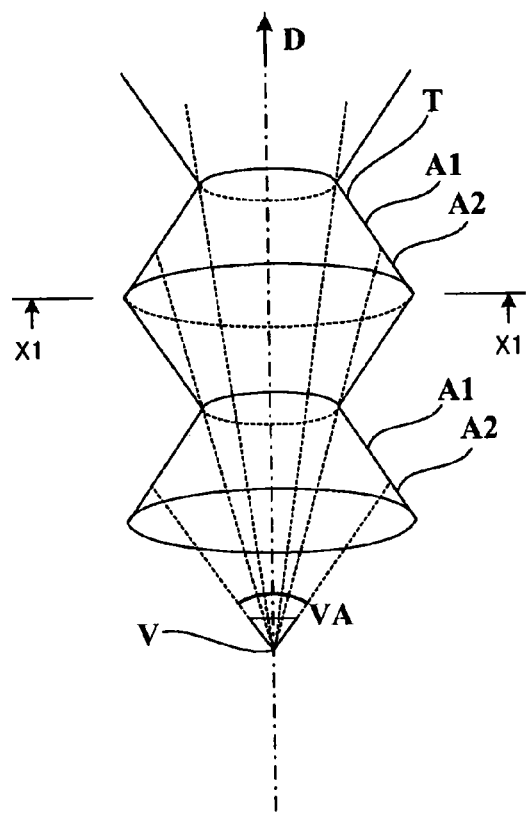
FIG. 3 is a diagram showing the observation region and non-observation region.

FIG. 3 is a diagram showing the observation region and non-observation region upon virtual endoscopy when observed from a particular view point location on the three-dimensional image. In FIG. 3, the angular field of the view is indicated by VA.

As shown in FIG. 3, assuming that light rays are irradiated from the view point location V to a view direction D with the designated view angle VA, a region in which light hits and a region in which light does not hit are made in the inner wall of the tubular body T. The former is indicated as the observation region A1. The latter is indicated as the non-observation region A2.

The observation region calculating unit 13 obtains the observation region A1 in the inner wall of the tubular body T based on the three-dimensional image and observation information corresponding to the inner wall of the tubular body T. The storage (for example, the internal storage of medical image processing apparatus) stores by associating the obtained observation region A1 with the observation information.

(Non-Observation Region Calculating Unit)

Next, the non-observation region calculating unit 14 is described.

The non-observation region calculating unit 14 obtains the non-observation region at the same timing as the observation region calculating unit 13.

The non-observation region calculating unit 14 obtains the non-observation region based on the observation region A1 obtained from the observation region calculating unit 13. Here, the non-observation region comprises a region that is not observed among the virtual endoscopic images currently being displayed and the region that has not yet been displayed as the virtual endoscopic image (region before observation). The non-observation region calculating unit 14 obtains the non-observation region A2 in the inner wall of the tubular body T based on the three-dimensional image and observation region A1 corresponding to the inner wall of the tubular body T. Here, when the overall region of the inner wall of the tubular body T is A0, the region excluding the observation region A1 from the overall region A0 becomes the non-observation region A2 (A2=A0−A1). The storage associates the obtained non-observation region A2 with the observation information and stores them.

Furthermore, the non-observation region calculating unit 14 may obtain the non-observation region based on the observation information regarding the three-dimensional image of the tubular body T and the virtual endoscopic image in the same manner as the observation region calculating unit 13.

(MPR Image Generating Unit)

The MPR image generating unit 12 generates the MPR image of the tubular body cut at a specified cross-section.

Examples of the specified cross-section include an axial cross-section (AP shown in FIG. 2), sagittal cross-section (SP shown in FIG. 2), and coronal cross-section (CP shown in FIG. 2). Moreover, the MPR images of the axial cross-section, coronal cross-section, and sagittal cross-section may be referred to as an axial image, coronal image, and sagittal image, respectively.

The MPR image generating unit 12 generates the MPR image based on the three-dimensional image stored in the storage 1 and the supplementary information associated with the virtual endoscopic images obtained from the virtual endoscopic image generating unit 11. Examples of supplementary information include the view point location, view direction, and view angle of the virtual endoscopic images. The supplementary information may be referred to as observation information. The MPR image mentioned here may refer to the MPR image of the observation region and/or the non-observation region, the MPR image combining this region and the tubular body, or the MPR image of the tubular body.

As shown in FIG. 2, the view point location V is the intersection point of the axial cross-section AP, sagittal cross-section SP, and coronal cross-section CP. Thereby, the view point location V of virtual endoscopy may be displayed at any cross-section.

Moreover, as shown in FIG. 2, the cross-section perpendicular to the view direction D is determined as the axial cross-section AP. Furthermore, the cross-section comprising the gaze LV perpendicular to each other are determined as the sagittal cross-section SP and the coronal cross-section CP. Thereby, the inside of the tubular body being observed may be observed in a deep direction upon virtual endoscopy. Furthermore, the intersection-point of the axial cross-section AP, sagittal cross-section SP, and coronal cross-section CP, as well as the information comprising the view direction D, axial cross-section AP, sagittal cross-section SP, and coronal cross-section CP may be referred to as the image information of the MPR image.

The MPR image generating unit 12 may generate the MPR image of the tubular body in each cross-section among the axial cross-section AP, sagittal cross-section SP, and coronal cross-section CP based on the crossing-point of the axial cross-section AP, sagittal cross-section SP, and coronal cross-section CP as well as the view direction D. Furthermore, the view point location V is included in the MPR images of all tubular bodies.

Figure 4:
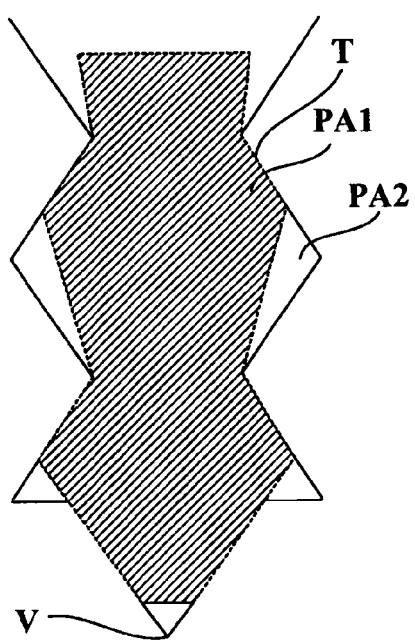
FIG. 4 is a diagram showing the observation region and non-observation region of the coronal cross-section.

FIG. 4 is a diagram showing the observation region and non-observation region of the sagittal cross-section SP. FIG. 4 shows the region PA1 corresponding to the observation region A1 as well as the region PA2 corresponding to the non-observation region A2 of the sagittal cross-section SP. Furthermore, the observation region A1 and non-observation region A2 of the coronal cross-section CP are also displayed in the same manner as FIG. 4.

Figure 5:
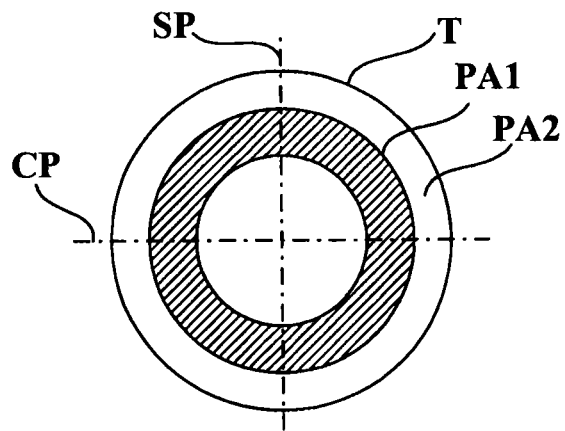
FIG. 5 is a diagram showing the observation region and non-observation region of the axial cross-section.

FIG. 5 is a diagram showing the axial image of the cross-section (axial cross-section AP) of the X1-X1 line in FIG. 3. FIG. 5 shows the region PA1 corresponding to the observation region and the region PA2 corresponding to the non-observation region of the axial cross-section AP.

As shown in FIG. 4 and FIG. 5, the MPR image generating unit 12 generates the MPR image (image of the region PA1) of the observation region A1 of each cross-section of the axial cross-section AP, sagittal cross-section SP, and coronal cross-section CP based on the observation region A1 read-out from the storage. The storage stores the generated MPR image of the observation region A1

The MPR image generating unit 12 generating an MPR image of the observation region A1 was described; however, the MPR image generating unit 12 may generate an MPR image of the non-observation region A2. That is, the MPR image generating unit 12 generates an MPR image (image of the region PA2) of the non-observation region A2 of each cross-section of the axial cross-section AP, sagittal cross-section SP, and coronal cross-section CP based on the non-observation region A2 read-out from the storage. The storage stores the generated MPR image of the non-observation region A2. Moreover, the MPR image of the non-observation region PA2 of, for example, the sagittal cross-section SP, is generated as a region excluding the region PA1 from the overall region PA0 of the MPR image (PA2=PA0−PA1).

In the above, the MPR image generating unit 12 was shown as an image generating unit that generates an MPR image that combines the observation region and/or the non-observation region and the tubular body, as well as the MPR image of the tubular body; however, it is not limited to this. The image generated from the image generating unit may be an image made using a curved MPR (curved planar reconstruction: CPR), which is a method of re-constructing along a meandering surface and a curved surface. CPR images are used when observing along the curved surface of a tubular body such as the colon, blood vessels, etc.

(GUI)

The GUI 20 comprises an input unit 21, a display control unit 22, and a display unit 23. Examples of the input unit 21 include pointing devices such as a mouse, joystick, touch panel, etc.

The display control unit 22 displays the observation region A1 and/or non-observation region A2 of the virtual endoscopic images on the display unit 23 as MPR images.

[Operation]

Figure 6:
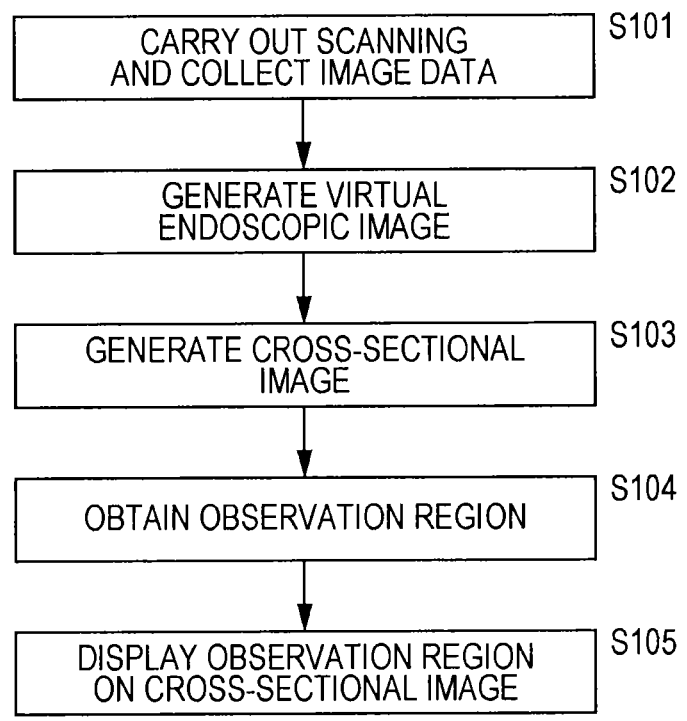
FIG. 6 is a flow chart showing a series of actions of the medical image processing apparatus.

Next, a series of operations of the medical image processing apparatus is described with reference to FIG. 6. FIG. 6 is a flow chart showing a series of actions of the medical image processing apparatus.

(S101)

In S101, a contrast agent is administered to the vessel upon CT so that the lesion candidate of the subject may be clearly rendered, inspection is carried out by changing the CT value between tissues, and an inspection is carried out with the colon is expanded by inserting carbon dioxide inside the colon. The three-dimensional image collected upon CT is stored in the storage 1.

(S102)

In S102, the virtual endoscopic image generating unit 11 generates virtual endoscopic images when the inside of the tract is observed based on the three-dimensional image of the tubular body and observation information including the intratubular view point location, view direction, and view angle placed in the tubular body. The three-dimensional image of the tubular body is stored in the storage 1.

(S103)

In S103, the MPR image generating unit 12 generates MPR images that cut the tubular body at each cross-section of the axial cross-section AP, sagittal cross-section SP, and coronal cross-section CP. Thereby, an MPR image of each cross-section of the axial cross-section AP, sagittal cross-section SP, and coronal cross-section CP may be obtained.

(S104)

In S104, the observation region calculating unit 13 obtains the observation region A1 of the inner wall of the tubular body T based on the image information of the three-dimensional image of the inner wall of the tubular body T and the observation information (the view point location V, view direction D, and view angle) in the virtual endoscopic images.

Furthermore, the non-observation region calculating unit 14 may obtain the non-observation region. In such cases, the non-observation region calculating unit 14 obtains the non-observation region A2 of the inner wall of the tubular body T based on the image information of the inner wall of the tubular body T and the observation region A1. Here, if the overall region of the inner wall of the tubular body T is A0, the region excluding the observation region A1 from the overall region A0 becomes the non-observation region A2 (A2=A0−A1).

Furthermore, the MPR image generating unit 12 obtains the regions PA1 that is the observation region A1 and that are included in the axial cross-section AP, sagittal cross-section SP, and coronal cross-section CP, respectively.

Furthermore, in the non-observation region A2, the regions PA2 comprised in the axial cross-section AP, sagittal cross-section SP, and coronal cross-section CP may be respectively obtained. Regarding the MPR image as well, the region excluding the region PA1 from the overall region PA0 of the MPR image becomes the region PA2 (PA2=PA0−PA1).

(S105)

In S105, the MPR image generating unit 12 colors the regions PA1 and PA2 obtained in S104. The display control unit 22 displays images of the colored regions A1 and A2 as MPR images.

Moreover, the MPR image generating unit 12 moves and/or rotates the view direction D in the MPR image based on the observation information of the virtual endoscopic images and the image information of MPR images, thereby aligns with the view direction D in the virtual endoscopic images, and the view point location V in the MPR image corresponding to the view point location V in the virtual endoscopic images is further obtained. The display control unit 22 displays the view point location V on the MPR images.

The regions A1 and A2 as well as the view point location V are displayed regarding the axial cross-section AP, sagittal cross-section SP, and the coronal cross-section CP, respectively.

The effect obtained from the series of operations of the medical image processing apparatus described above is described with reference to FIGS. 7A to 8B.

Figure 7A:
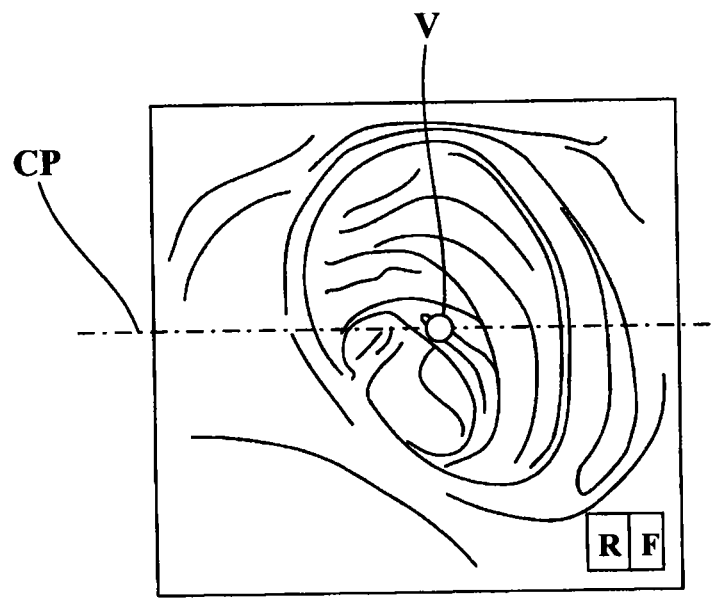
FIG. 7A is a diagram showing a virtual endoscopic image.
Figure 7B:
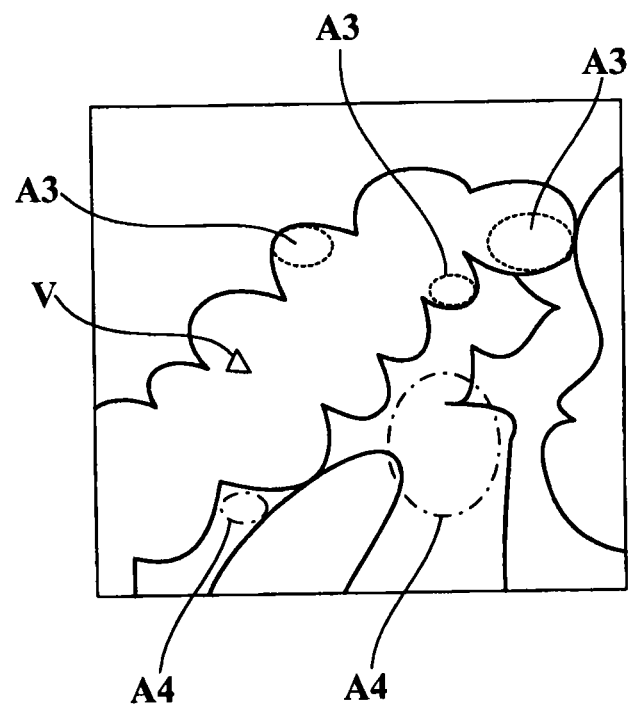
FIG. 7B is a diagram showing an MPR image.
Figure 7C:
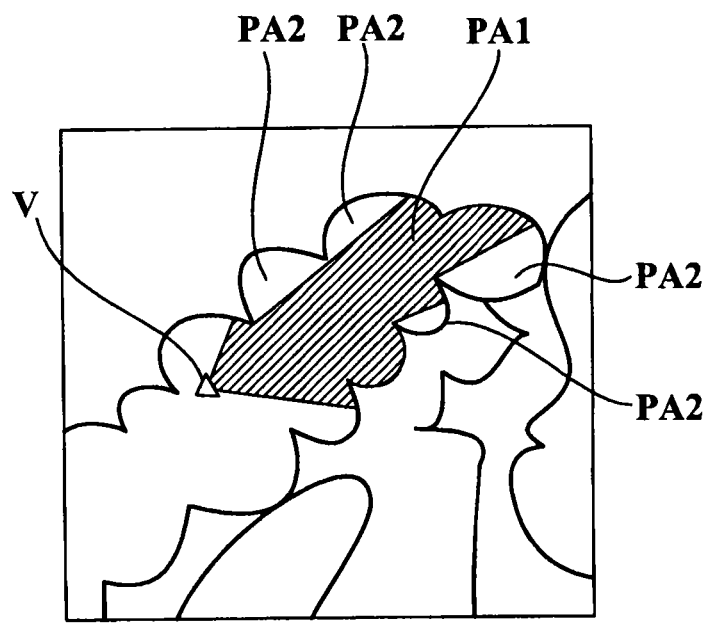
FIG. 7C is a diagram showing an MPR image.

FIGS. 7A to 7C are diagrams showing the display example of the region observed upon virtual endoscopy and the region that may not be observed. FIG. 7A is a diagram showing the virtual endoscopic images, FIG. 7B is a diagram showing the MPR image, and FIG. 7C is a diagram showing the MPR image. In FIG. 7A, the view point location V and coronal cross-section CP are displayed in the center of the virtual endoscopic images. Moreover, in FIG. 7B, the view point location V is displayed in the MPR image. Furthermore, in FIG. 7C, the view point location V and the region PA1 corresponding to the observation region A1 observed in the virtual endoscopic images are displayed in the MPR image.

As shown in the MPR image of FIG. 7B, the user predicts the region PA1 corresponding to the observation region A1 that is observed in the virtual endoscopic images and the region PA2 corresponding to the non-observation region A2 that is not displayed in the virtual endoscopic images due to blind spots, etc. based on the view point location V displayed in the MPR images, and distinguishes the two according to this; therefore, distinguishing the two regions become difficult. Furthermore, distinguishing the two regions becomes even more difficult because the outside of the observation region is displayed.

With respect to this, as shown in the MPR image of FIG. 7C, the region PA1 corresponding to the observation region A1 was displayed as the MPR image, so the user may easily distinguish the observation region A1 and the non-observation region A2.

Figure 8A:
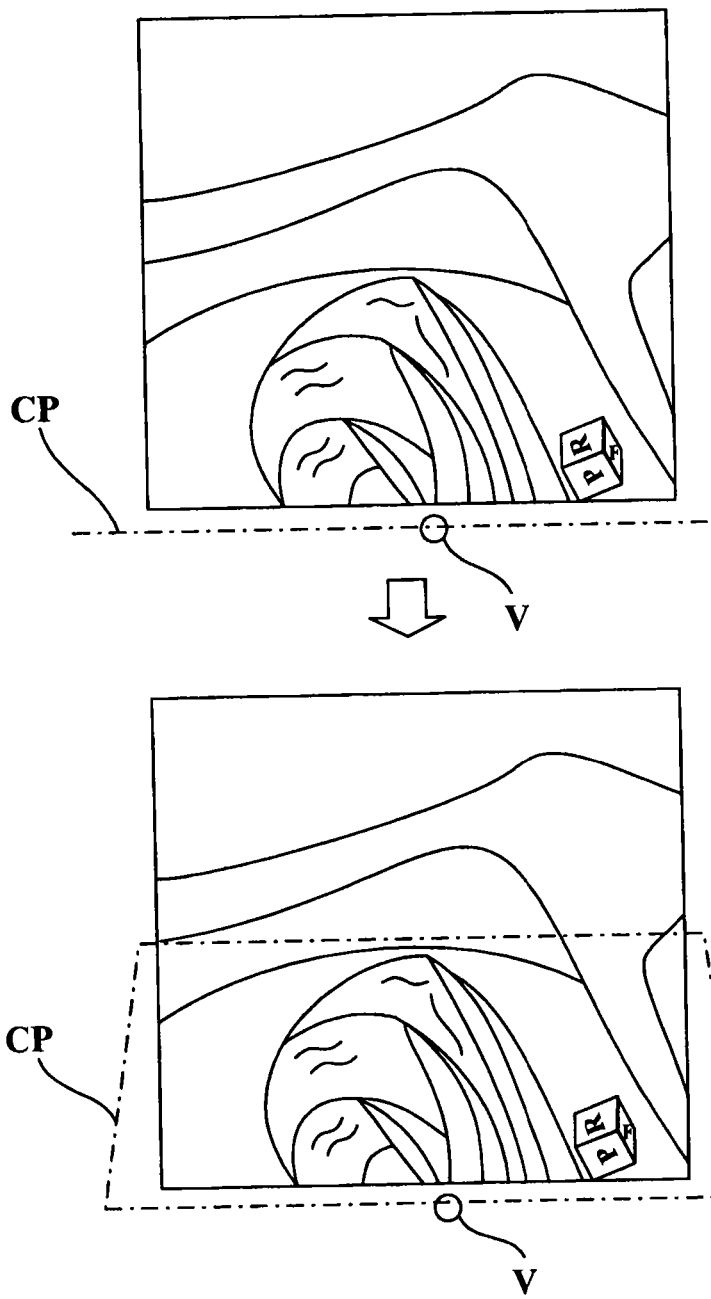
FIG. 8A is a diagram showing a group of a virtual endoscopic image and an MPR image.

FIGS. 8A and B are diagrams showing examples in which the regions currently being observed are displayed as MPR images. FIG. 8A shows the combination of virtual endoscopic images and the MPR images of the coronal cross-section. The view point location V is displayed at the end of the virtual endoscopic images, and the coronal cross-section CP that does not contact the virtual endoscopic image (does not intersect) is displayed. Thereby, only the view point location V is displayed in the MPR image and the region PA1 corresponding to the observation region A1 is not displayed. Consequently, distinguishing the currently observed region is difficult by merely displaying the view point location V.

Figure 8B:
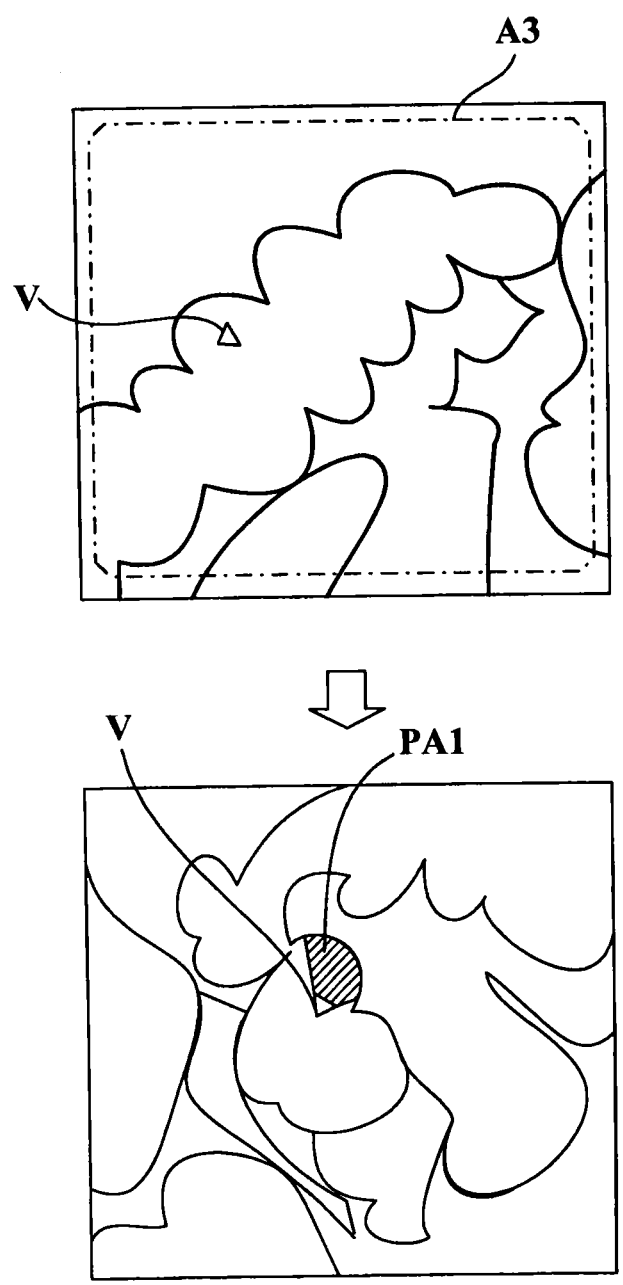
FIG. 8B is a diagram showing a group of a virtual endoscopic image and an MPR image.

FIG. 8B shows the combination of a virtual endoscopic image and an MPR image of the coronal cross-section. Although the view point location V is displayed at the end of the virtual endoscopic image, the coronal cross-section CP is displayed contacting the virtual endoscopic image (so as to intercross). Thereby, the region PA1 corresponding to the observation region A1 is displayed in the MPR image in addition to the view point location V.

The display control unit 22 displays the observation region A1 generated as a cross-sectional image by the cross-sectional image generating unit 12 based on the observation information. For example, as shown in FIG. 8A, the observation region A1 being observed was displayed as the MPR image by changing the view direction (location of the coronal cross-section CP), so that whether or not the region is currently being observed may be easily differentiated.

In this manner, the observation region A1 synchronizing with the observation information including the view direction was displayed as the MPR image; thereby, it is possible to carry out effective preoperative diagnosis (including screening test).

[Embodiment 2]

Next, the medical image processing apparatus related to Embodiment 2 is described. Furthermore, in the configuration of the medical image processing apparatus, the configuration differences between Embodiment 2 and Embodiment 1 are mainly described, the descriptions regarding those that are the same omitting by attaching the same number.

As shown in FIG. 1, the difference with Embodiment 2 is that it is provided with an observation information setting unit 15 that sets the observation information including the view point location V, view direction, and view angle, so as to allow for observation of the non-observation region.

(Observation Information Setting Unit)

The observation information setting unit 15 sets at least one or two or more combinations among the view point location V, view direction, and view angle such that the non-observation region may be observed. The set observation information is stored in the storage (for example, internal storage of the medical image processing apparatus).

Figure 9:
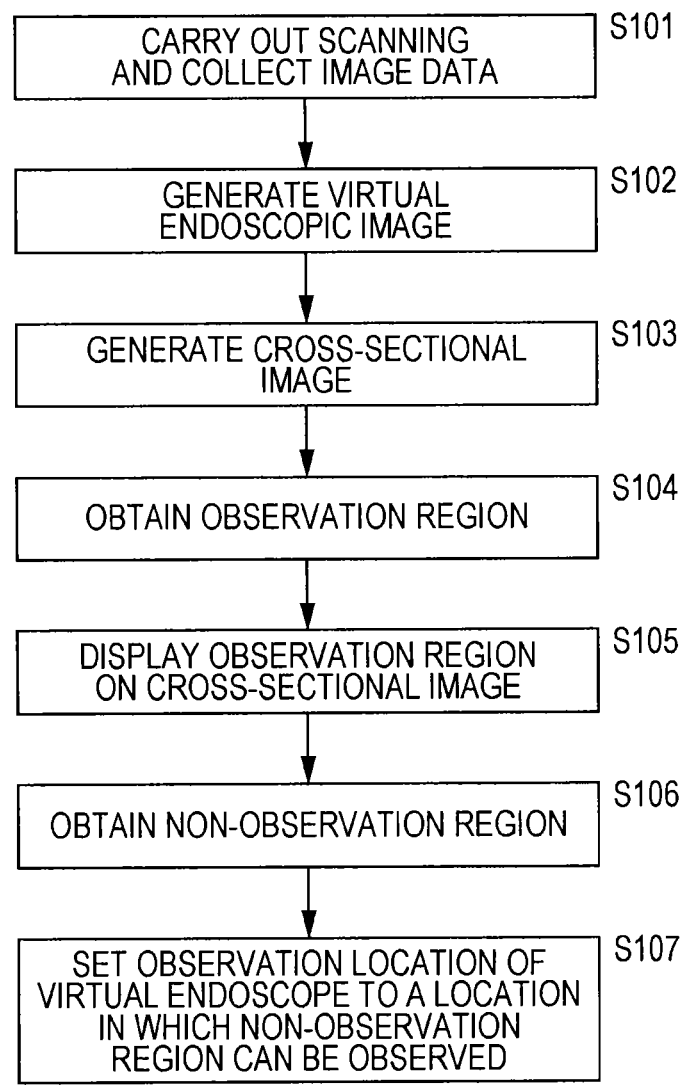
FIG. 9 is a flow chart showing a series of actions of the medical image processing apparatus related to Embodiment 2.

Next, the series of operations of the medical image processing apparatus is described with reference to FIG. 9. FIG. 9 is the flow chart showing a series of actions of the medical image processing apparatus.

(S101) to (S105)

As may be understood by comparing FIG. 9 and FIG. 6, Embodiment 2 is the same as Embodiment 1 in operations S101 to S105, so descriptions on the operations thereof are omitted.

Figure 10A:
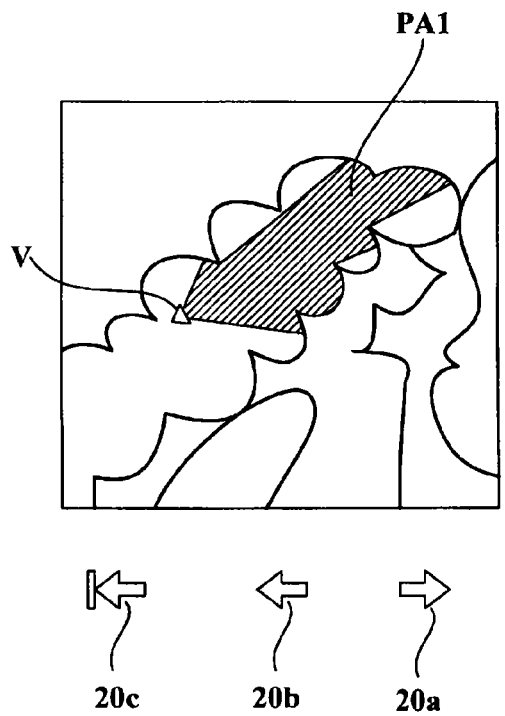
FIG. 10A is a diagram showing the MPR image when the screening test is stopped.
Figure 10B:
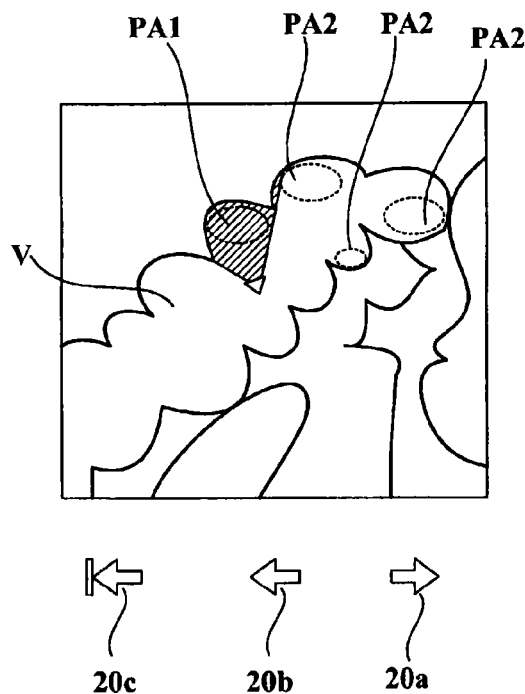
FIG. 10B is a diagram showing the MPR image when confirming the non-observation region.
Figure 10C:
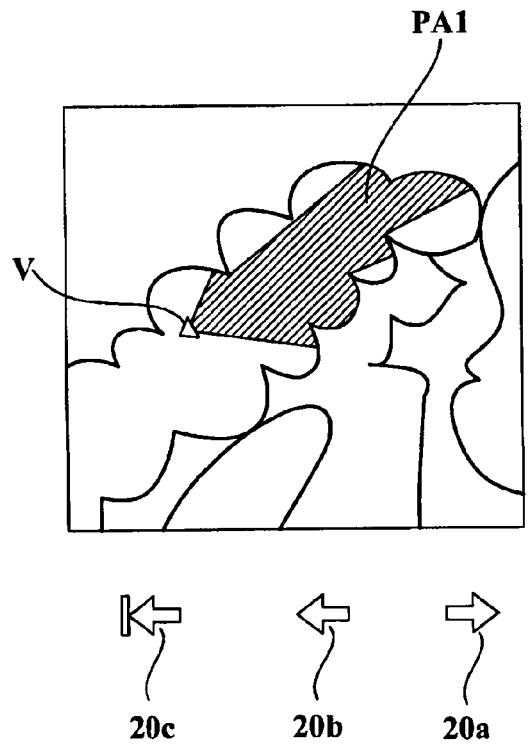
FIG. 10C is a diagram showing the MPR image when the screening test is re-started.

FIG. 10A is a diagram in which the screening is stopped, FIG. 10B is a diagram in which the non-observation region is observed, and FIG. 10C is a diagram in which the screening is re-started. In FIGS. 10A to 10C, as an example of the GUI20, a forward button, return button, return to the current location button are displayed as "20a", "20b", and "20c", respectively. From the designations of each button 20a, 20b, and 20c by a clicking operation of the mouse, the display control unit 22 displays the non-observation region A2 regarding the next view point location, the previous view point location, and the current view point location (view point location before shifting) in an order determined in advance. The non-observation region A2 may be confirmed using each button 20a, 20b, and 20c.

When temporarily stopping the screening test and confirming the non-observation region A2 that cannot be observed from the current view point location V due to the lesion candidate, blind spot, etc., the following procedures are taken.

(S106)

In S106, the non-observation region A2 that cannot be observed from the current view point location V due to the lesion candidate, blind spot, etc. is calculated.

The observation region calculating unit 13 calculates the tubular body (overall) A0 observed that is displayed on the MPR image based on the observation information (view point location V, view direction D, view angle VA), which is the supplementary information of the virtual endoscopic images, and the image information of MPR images.

Next, the MPR image generating unit 12 obtains the region PA1 of the observation region A1 included in the cross-section of the MPR images based on the observation region A1 obtained from the observation region calculating unit 13 and the image information of the MPR images. Moreover, the region PA0 of the tubular body (overall) included in the MPR image is obtained.

Next, the non-observation region calculating unit 14 calculates the non-observation region PA2 by subtracting the region PA1 comprised in the cross-section of the MPR images from the obtained tubular body (overall) PA0 (PA2=PA0−PA1).

Furthermore, the non-observation region A2 differs depending on the cross-section of the MPR images; therefore, when calculating the non-observation region A2, the cross-section of the MPR image must be identified by the GUI20 in advance.

(S107)

In S107, the observation information setting unit 15 obtains the observation information (view point location, view direction, and view angle) that may observe the non-observation region A2 obtained from the non-observation region calculating unit 14, and sets the observation information thereof (for example, storing to the internal storage of the medical image processing apparatus).

The GUI20 shifts the view point location V to a location in which the non-observation region A2 may be observed based on the set observation information. By means of shifting the view point location V in this manner, the non-observation region A2 may be observed without fail, so overlooking of the non-observation region A2 may be prevented without fail.

Furthermore, as shown in the MPR image of FIG. 10B, when there are several non-observation regions A2, the GUI20 shifts the view point location V to the respective location in which the non-observation region A2 may be observed in the order determined in advance. At this time, the GUI20 determines the view point location V closest to the view point location V during observation as the next view point location V from among the view point locations V that may observe the non-observation regions A2.

While shifting the view point location V, the relative relationship between the shifted view point location V and the view point location V being observed may be understood; therefore, the display control unit 22 continues to display the observation region A1 being observed on the MPR images.

By shifting the view point location V in order and after confirming all the non-observation regions A2, the view point location V is returned to the location before shifting, as shown in FIG. 10C.

Thereby, as may be understood from FIG. 10A and FIG. 10C, the non-observation region A2 is observed in the middle of the screening test; therefore, the screening test may be re-started continuously from the location before shifting even after the view point location V has been shifted.

As observed from the MPR images shown in FIG. 10B, the non-observation region A2 due to blind spots, etc. may be confirmed taking into consideration the view point location V upon virtual endoscopy, and overlooking of the non-observation region A2 upon the screening test may be prevented.

[Modified Example]

Next, the display example for preventing overlooking is described with reference to FIG. 11.

In the embodiment, the observation region being observed is described as an example to be displayed on the MPR images; however, in order to prevent overlooking of the region to be observed upon the screening test, the region that was previously observed may also be displayed on the MPR image. The displaying method is the same as the method used for the region currently being observed.

The region identifying means comprising the observation region calculating unit 13 and the non-observation region calculating unit 14 accumulates the observation region and non-observation region along with shifting of the view point location or view direction. For example, adding the observation region refers to adding the newly observed region to the region that has already been observed.

Moreover, for example, the accumulation of the non-observation region refers to adding a newly confirmed region to non-observation regions which have not yet been confirmed. For example, if the non-observation regions which has not yet been confirmed are determined as "PA21," "PA22," and "PA23" and when the non-observation region PA21 is determined as the newly confirmed region (−PA21) among these, the addition formula becomes PA21+PA22+PA23+(−PA21), and the result from addition becomes PA22+PA23. Thereby, the generation of the overlooked regions may be prevented.

Figure 11:
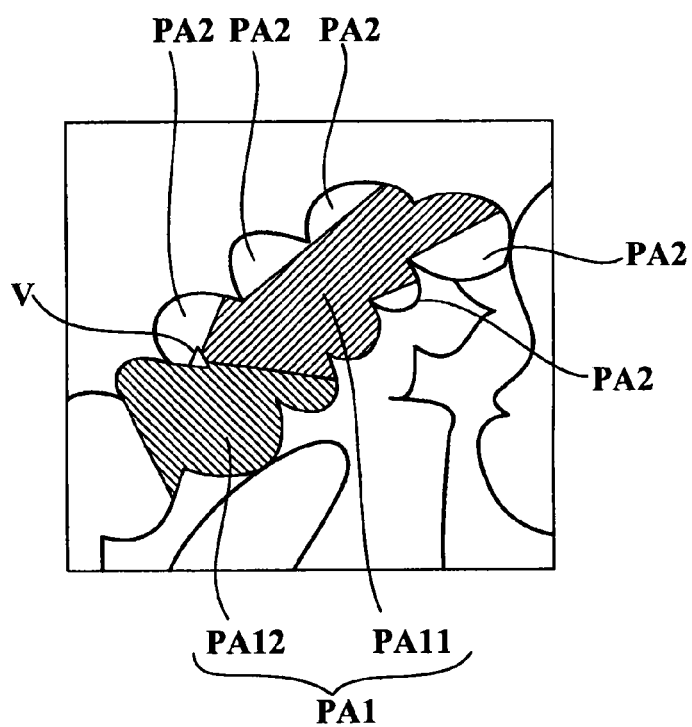
FIG. 11 is a diagram showing a display example for preventing overlooking.

FIG. 11 is a diagram showing a display example for preventing overlooking. As shown in FIG. 11, the region being observed PA11 and a region that has been observed PA12 may be distinguished by differentiating a display color. Furthermore, in FIG. 11, the color difference is shown by changing a hatching.

That is, the MPR image generating unit 12 generates the region being observed PA11 based on the view point location V during observation and the region PA1 included in the specified cross-section. The region subtracting the region being observed PA11 from the region PA1 becomes the region that has been observed PA12 (PA12=PA1−PA11).

The display control unit 22 displays the region being observed PA11 and the region that has been observed PA12 on the display unit 23. Furthermore, both regions PA11 and PA12 may be displayed with a different display pattern (pattern).

According to the embodiment explained above, a description is mentioned with the CT colonograph (CT Colonography) using CT as an example; however, recently, the usefulness of MR colonographs using an MRI is being reported, and the MR colonographs may also be used. The MR colonograph is also reported as a diagnostic method that improves problems of the CT colonograph (pain forced upon patients during pretreatment and tests, X-ray exposure, etc.), and an MR colonograph with higher resolution is expected in the future.

The embodiment of the medical image processing apparatus was described above; however, it may be a CT comprising this medical image processing apparatus or other modifications thereof (medical image diagnosis apparatus).

Moreover, in the embodiment, the observation region and/or the non-observation region was displayed on the MPR images; however, it may be displayed on the three-dimensional images. Here, as an example of the three-dimensional images, volume rendering in which various coloring is carried out according to the CT value of each CT image and which displayed by overlaying multiple successive CT images.

The observation region and non-observation region may be displayed on the image to allow distinguishing. For example, when displaying the non-observation region on the three-dimensional image, instead of displaying the overall non-observation region, the presence of the non-observation region may be displayed, allowing distinguishing of the presence of the non-observation region by adding, for example, a mark in the center location of the non-observation region. This is because, when the overall non-observation region is displayed on the three-dimensional image, the non-observation regions overlap each other and the location and size of each non-observation region becomes difficult to distinguish.

Furthermore, in the embodiment, the observation region and/or non-observation region were obtained based on the observation information (view point location, view direction, view angle) of the virtual endoscopic images; however, these regions may be obtained based on the view point location and view direction.

Several embodiments of the present invention were described; however, these embodiments were presented as examples and are not intended to limit the range of the invention. These new embodiments may be carried out in various other forms, and various abbreviations, revisions, and changes may be carried out within a range not deviating from the gist of the invention. These embodiments and modifications thereof are within the range and gist of the invention while also being included within the range of the invention described in the range of the patent claims and the equivalent thereof.

EXPLANATION OF SYMBOLS 1 storage
11 virtual endoscopic image generating unit
12 MPR image generating unit
13 observation region calculating unit
14 non-observation region calculating unit
15 observation information setting unit
20 GUI
21 input unit
22 display control unit
23 display unit

What is claimed is:

1. A medical image processing apparatus, comprising:
a storage that stores three-dimensional images of a tubular body;
a virtual endoscopic image generator, implemented by circuitry, that generates, by using the three-dimensional images of the tubular body, virtual endoscopic images of an inside of a tract of the tubular body according to a view point location and a view direction inside the tract of the tubular body, the virtual endoscopic images including a virtual endoscopic image of an observation region;
a region identifier, implemented by the circuitry, that determines the observation region, the observation region including a volume from the view point location along a line-of-sight of the view direction to the tract of the tubular body ; and
an image generator, implemented by the circuitry, that generates a cross-sectional image of the tubular body indicating the observation region, the cross-sectional image being distinguishably displayed on a virtual endoscopic image of the virtual endoscopic images obtained from the three-dimensional images, wherein
an area representing the observation region is superimposed on the cross-sectional image, and the area is filled to distinguish the observation region in the tubular body.

2. The medical image processing apparatus according to claim 1, wherein
the region identifier further determines the observation region based on a view angle in addition to the view point location and the view direction.

3. The medical image processing apparatus according to claim 1, wherein
the region identifier further determines a non-observation region inside the tract of the tubular body, the non-observation region including a difference between a volume inside the tract of the tubular body and the observation region,
the region identifier is further configured to determine a shift of the view point location and the view direction whereby a first portion of the non-observation region is within line-of-sight of the shifted view point location and the shifted view direction, and the virtual endoscopic images generated by the image generator further includes a virtual endoscopic image of the first portion of the non-observation region.

4. The medical image processing apparatus according to claim 3, wherein the region identifier is further configured to add the first portion of the non-observation region to the observation region and subtract the first portion of the non-observation region from the non-observation region after the shifting of the view point location and the view direction.

5. The medical image processing apparatus according to claim 1, further comprising:

an observation information adjuster, implemented by the circuitry, that determines another view point location and another view direction to obtain a virtual endoscopic image of the non-observation region and adjusts the view point location and the view respectively to be the another view point location and the another view.

6. The medical image diagnosis apparatus, comprising the medical image processing apparatus according to claim 1 and an image obtaining unit implemented by the circuitry.

7. A medical image processing apparatus, comprising:

a storage that stores three-dimensional images of the tubular body, a virtual endoscopic image generator, implemented by circuitry, that generates, by using the three-dimensional images of the tubular body, a virtual endoscopic image of an inside of a tract of the tubular body according to observation information, the observation information including a view point location and a view direction inside the tract of the tubular body, a cross-sectional image generator, implemented by the circuitry, that generates a cross-sectional image of the tubular body based on the observation information, and a display controller that distinguishably displays, using a filled area superimposed on the cross-sectional image, at least one of an observation region and a non-observation region of the virtual endoscopic image on the cross-sectional image, the observation region including a volume from the view point location along a line-of-sight to the view direction to the tract of the tubular body, and the non-observation region including a difference between a volume inside the tract of the tubular body and the observation region.

8. The medical image processing apparatus according to claim 7, wherein the display controller reads the observation region that has already been observed from the storage, and displays the observation region.

9. The medical image processing apparatus according to claim 7, further comprising an observation region calculator, implemented by the circuitry, that calculates the observation region of the virtual endoscopic image based on the observation information.

10. The medical image processing apparatus according to claim 7, further comprising a non-observation region calculator, implemented by the circuitry, that calculates the non-observation region of the virtual endoscopic image based on the observation information.

11. The medical image processing apparatus according to claim 10, further comprising an observation information adjuster, implemented by the circuitry, that adjusts one or more among the observation information of the view point location, the view direction, and a view angle to enable observation of virtual endoscopic images of the non-observation region.

12. The medical image processing apparatus according to claim 9, wherein the display controller displays the adjusted observation information superimposed on the cross-sectional image.

13. The medical image processing apparatus according to claim 7, further comprising:

an observation information adjuster, implemented by the circuitry, that determines another observation information to obtain a virtual endoscopic image of the non-observation region, wherein the display controller adjusts the view point location to a view point location of the another observation information.

* * * * *